United States Patent [19]
Swinger

[11] Patent Number: 5,647,865
[45] Date of Patent: Jul. 15, 1997

[54] CORNEAL SURGERY USING LASER, DONOR CORNEAL TISSUE AND SYNTHETIC MATERIAL

[76] Inventor: Casimir A. Swinger, 9 W. 67th St., New York, N.Y. 10023

[21] Appl. No.: 786,397

[22] Filed: Nov. 1, 1991

[51] Int. Cl.$^6$ .................................................. A61N 5/06
[52] U.S. Cl. .................... 606/5; 606/3; 606/10; 128/898
[58] Field of Search .................. 128/395, 397, 128/398, 897–898; 606/2–19; 607/88, 89

[56] References Cited

U.S. PATENT DOCUMENTS

| | | | |
|---|---|---|---|
| 4,729,372 | 3/1988 | L'Esperance | 606/5 |
| 4,732,148 | 3/1988 | L'Esperance, Jr. | 606/5 |
| 4,840,175 | 6/1989 | Peyman | 128/898 |
| 4,903,695 | 2/1990 | Warner | 606/5 |

OTHER PUBLICATIONS

Brightbill, F.S., "Corneal Surgery", pp. 416–427 and pp. 480–497 (1986) C.V. Mosby.

Sanders, D.R., Hoffman, R.F., Saaz, J.J. "Refractive Corneal Surgery", pp. 467–548 (1985) Slack, Inc. Thorofare, N.J.).

*Primary Examiner*—David M. Shay

[57] ABSTRACT

Laser ablation is applied to a patient's cornea in a circumscribed fashion, while controlling energy flux, beam exposure diameter and exposure time to achieve removal of a central corneal disc of tissue in a volumetric fashion. The concavity produced is filled in with donor corneal tissue to effect restoration of the anterior cornea, both anatomically and optically, as may be required in removing an anterior corneal opacity. In addition, the patient's ablated corneal bed or the posterior donor corneal stroma may have optical refractive power imposed upon it, thereby affecting correction of optical errors of the eye, such as myopia, hyperopia, astigmatism, optical aberrations or combinations thereof, upon placement of the donor tissue within the patient's bed. Synthetic material, fashioned appropriately, may also be used to cover the patient's exposed corneal bed, or placed on the bed and covered with donor tissue to achieve correction of these same optical errors.

8 Claims, 6 Drawing Sheets

LASER BEAM – 1A

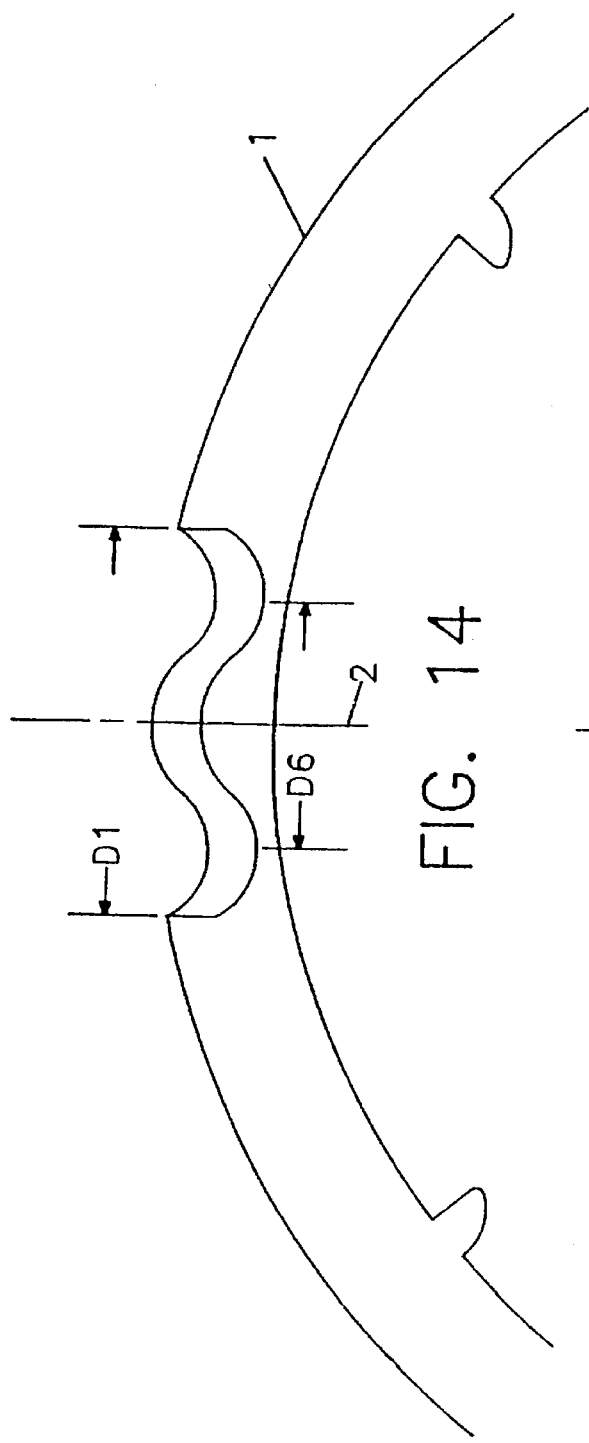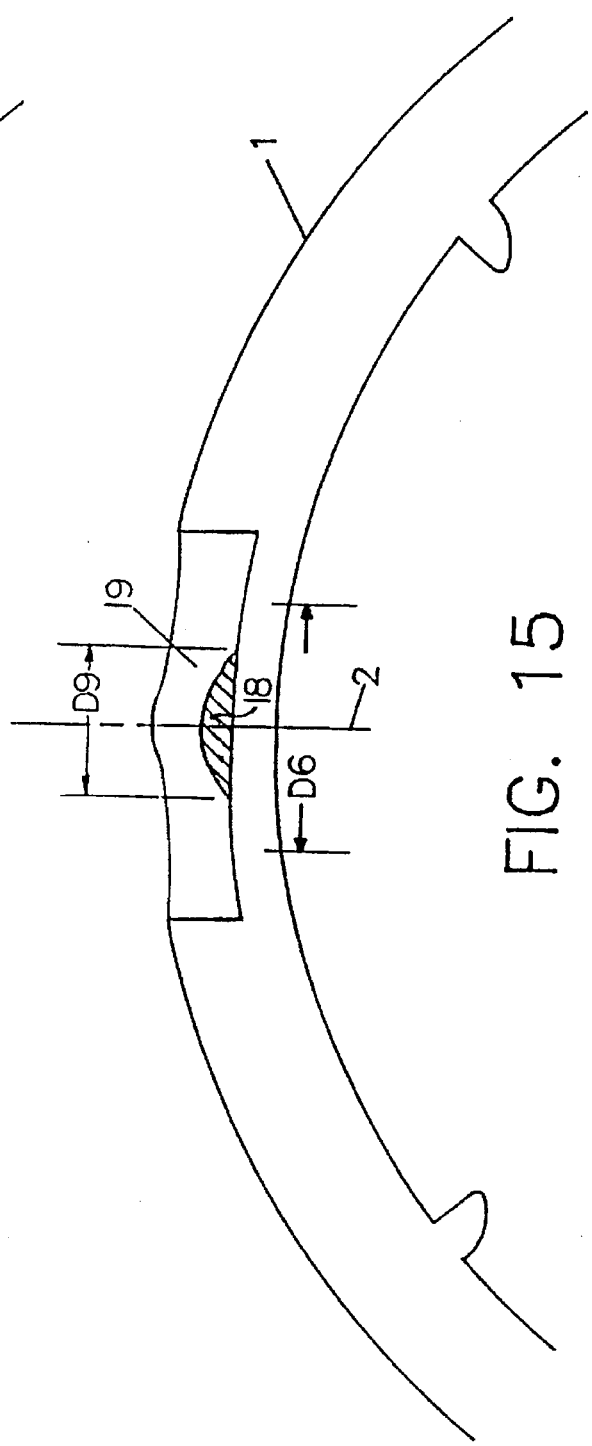

CORNEAL SURGERY USING LASER, DONOR CORNEAL TISSUE AND SYNTHETIC MATERIAL

BACKGROUND OF THE INVENTION

The invention relates to surgical procedures on the anterior aspect of the cornea of the eye. Such procedures include the operation of lamellar keratoplasty, designed to remove scarred, irregular or opaque corneal tissue from across the visually critical central optic zone of the cornea and replacement with a partial donor cornea to restore the corneal shape and clarity, thereby improving vision. It relates also to other operations on the anterior cornea designed primarily to produce changes in the optical imaging of the cornea, thereby correcting optic errors of the eye, such as myopia (nearsightedness), hyperopia (farsightedness), astigmatism, optical aberrations and combinations thereof.

The operation of partial thickness lamellar keratoplasty to remove corneal opacities has been practiced for many years (see Brightbill, FS, Corneal Surgery, Chapter 33, C.V. Mosby Co., St. Louis, 1986). It has classically been performed by direct mechanical removal of a circular disc of tissue of constant thickness and replacement thereof with a similarly shaped piece of donor corneal tissue. The optical quality of the final cornea has frequently been known to be irregular or with some interface opacity, and often results in reduction of vision from normal. More recently, this procedure has been performed with a high-speed microkeratome to effect detachment of the anterior disk both from the patient's cornea and from the donor's cornea.

Barraquer teaches the general art of altering the anterior corneal curvature of the eye to effect changes in refraction, or optical imaging of the eye, with the operation of keratomileusis, a form of lamellar keratoplasty. (See IBID, Chpt. 37). In this procedure, a circular lamellar disc of constant thickness centered on the visual axis is removed from the front of the patient's cornea with a high-speed microkeratome. Following said removal, called a lamellar keratectomy, the resected lamellar disc of constant thickness is placed onto one of two available devices (Barraquer cryolathe, BKS device) to effect modification in shape to produce a lenticule with refractive optical power. Although operationally different, both devices effect the production of a refractive corneal lenticule. The lenticule is produced by volumetric mechanical removal of stromal tissue from the cut and exposed corneal stromal surface of the resected lamellar disc. Such tissue removal may be greatest in the center of the disc, which allows for correction of myopia, or toward the outer periphery, which allows for correction of hyperopia. In any event, the tissue removal is usually such that there is a smooth and regular transition of thickness as one traverses the optically modified (optic zone) area. Following tissue removal from the disc (now called a lenticule), it is replaced onto the patient's cut stromal surface remaining behind after the initial keratectomy. Said replacement results in a new anterior corneal curvature and alteration in the optic imaging of light by the cornea.

The inventor teaches the possibility of accomplishing the same while utilizing donor corneal tissue to receive the volumetric optic cut. This allows for the tissue lenses to be manufactured in advance by someone other than the operating surgeon.

U.S. Pat. No. 4,732,148, L'Esperance, issued Mar. 22, 1988, discloses a method of applying ultraviolet radiation to the anterior cornea (photorefractive keratectomy) in order to correct the optical errors of myopia, hyperopia, and astigmatism. Unfortunately, the delicate anterior membrane complex of the patient's cornea (primarily Bowman's membrane) is destroyed in the process, leaving a cornea which is anatomically, and perhaps physiologically, abnormal. In addition, two other drawbacks of this method have been noted. The first is the production of haze within the operated cornea, which lasts for months, and which may be associated with visual symptoms or reduction in vision. Second, the anatomically abnormal cornea develops a healing response such that the outermost epithelial layer, regenerated over the operated area from peripheral unoperated epithelium, frequently demonstrates hyperplasia or thickening postoperatively. This can cause gross inaccuracy or instability of the obtained optical result.

Furthermore, it discloses a method of performing a corneal transplant operation with an ultraviolet laser, using donor tissue, whereby a refractive error may be simultaneously corrected. In this approach, laser irradiation is applied in a constant fashion to the anterior cornea of the patient such that a circular disc of constant thickness is ablated. A disc of comparable diameter but greater thickness is fashioned from a human donor cornea, with the anterior membrane complex intact. The donor disc is then placed into the recipient opening and sutured. Following this, the laser is applied to the front surface of the donor cornea, now part of the patient's cornea, and some of the front surface removed until the donor disc no longer protrudes above the patient's cornea. Also, optical power may be altered by ablating the front of the donor disc in a fashion that selectively alters the thickness of the donor disc in a controlled way. This method, also, has the undesirable result of damage to the anterior membrane complex of the cornea with resultant side effects as mentioned above.

U.S. Pat. No. 4,903,695, Warner at. al., issued Feb. 27, 1990 disclosed a method of performing Barraquer's keratomileusis operation using an ultraviolet or infrared laser to effect the tissue modification step, thereby replacing the cryolathe and BKS device. It also circumvents laser damage to the anterior cornea. However, the method requires the use of a mechanical microkeratome to first detach a circular disc of tissue from the patient's cornea. Following this mechanical cut, the laser irradiation is applied selectively to the cut stromal surface left behind on the patient to remove tissue in a controlled fashion such that when the initially resected disc is replaced onto the bed from which it was removed, a new curvature is imposed onto the anterior corneal surface.

The techniques described above have met with several shortcomings, as partly described. When the laser is used to remove a disc of scarred tissue from the patient's cornea and left to heal (called phototherapeutic keratectomy), this is followed by haze and hyperplasia of the epithelium, which causes undesirable hyperopia. Also, removal of deep pathology may cause greater haze and corneal instability, and is usually not attempted. The current invention solves both problems by restoring corneal thickness to approximately normal and providing an anterior membrane complex.

When the laser is used as above in Warner, et. al., to correct an optical error, the surgeon must use a microkeratome to first prepare the patient's cornea in anticipation of laser ablation. This instrument has been shunned by most surgeons who have used it due to technical difficulty in mastering it, irregular cuts, and deleterious visual sequellae in some cases.

The present invention allows for the performance of phototherapeutic and photorefractive keratectomy without the need for any complex mechanical cutting device, such as the microkeratome, in patient surgery while simultaneously providing a normal anterior membrane complex. To date, this has not been accomplished.

SUMMARY OF THE INVENTION

It is an object of the invention to provide an improved surgical technique for performance of operations such as lamellar keratoplasty, keratomileusis, photherapeutic and photorefractive keratectomy on the outer aspect of the cornea.

It is another object to simplify operations, as above, on the cornea to reduce optical (refractive) errors by obviating the need for cumbersome and complicated mechanical devices (such as the microkeratome, cryolathe and BKS device) from said surgery.

It is a specific object to achieve the preceeding objects by providing a procedure to reduce myopia, hyperopia, astigmatism, irregular astigmatism, presbyopia, optical aberrations of the eye such as spherical aberration, or any combinations thereof.

It is an object to provide an improved lamellar keratoplasty operation on the cornea by eliminating the need for the above mentioned mechanical devices.

It is an object to accomplish performance of the above mentioned surgical procedures while providing for a relatively normal anterior corneal structure in the critical central optic area at the conclusion of the procedure.

It is an object to accomplish the above by ultraviolet or other wavelength laser irradiation to the cornea, using any commercially available laser, with or without a beam control scanner.

The invention achieves the above objects by controlled laser ablation of the patient's cornea to remove a circular outer portion of constant thickness. The exposed surface may then be ablated in a zone of smaller diameter than the original ablation to impose optical power onto the surface, followed by placement of a donor corneal or synthetic material (examples of which include, but are not limited, to collagen and plastic) disc of diameter, and thickness similar to the original disc removed from the patient's cornea.

Alternatively, the donor disc alone may have the optical power imposed onto its bare stromal surface by laser ablation and, following this, the donor cornea is placed into the opening created in the patient's cornea, thereby altering the refractive power of the eye. In the case of lamellar keratoplasty optical power may or may not be imposed at either site. Or, a synthetic lens, with or without optical power, may be placed into the patient's recipient opening, on whose stromal bed optical power may or may not have been imposed by laser treatment. Or, upon placing a synthetic lens upon the exposed bed, said lens may be covered by a donor corneal disc without optical power.

BRIEF DESCRIPTION OF THE DRAWINGS

The invention will be described in detail with the assistance of the following drawings.

FIG. 14 is a view similar to FIG. 11 demonstrating hyperopic correction.

FIG. 15 is a view similar to FIG. 1 showing optical correction using a synthetic lens with optical power and a donor disc without power.

DETAILED DESCRIPTION OF THE DRAWINGS

Figure 1:
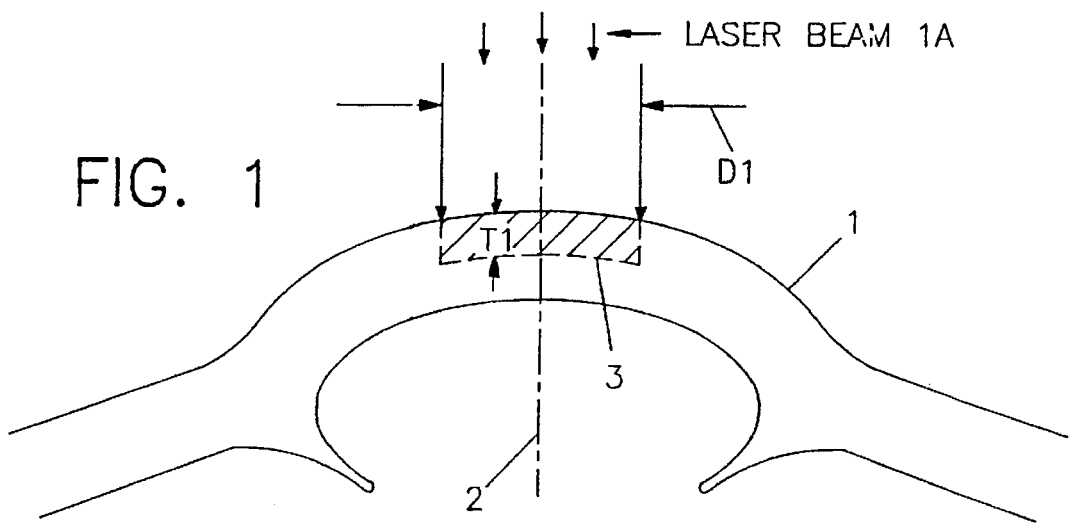
FIG. 1 is a simplified side view of the cornea, as an elevation in section through a plane intersecting and parallel to the visual axis as the plane 1 shown in FIG. 2, demonstrating the area of initial laser ablation.
Figure 2:
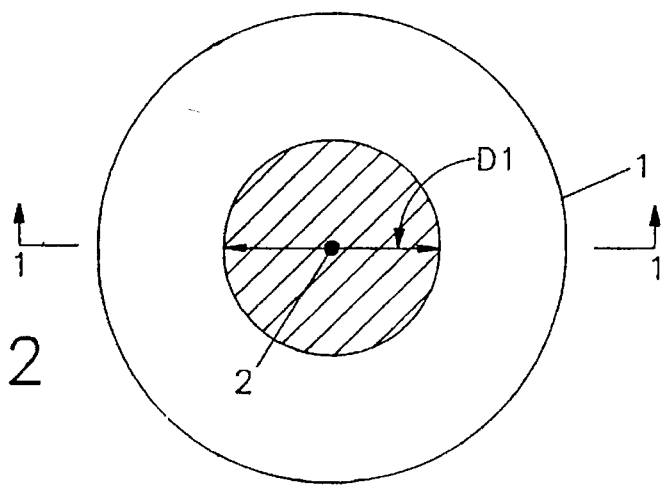
FIG. 2 is a front elevation of FIG. 1.

In FIGS. 1 and 2 the cornea 1 is to have laser irradiation 1a applied in a uniform circular disk-like manner (though not limited to circular as a non-circular surface profile, such as elliptical, may also be used), symmetrically centered on the visual axis, in a zone of diameter D1, less than the corneal diameter (approximately 12 mm) end greater than the optically used central zone, and to depth T1, about the line of sight or visual axis, 2. The determination of this axis is as with conventional surgery, as for radial keratotomy, and may be stabilized with respect to the laser beam by surgeon fixation with a pericorneal suction fixation Ping, direct patient visualization on a fixation light oriented appropriately to the laser beam, or by a tracking system. Such methods are current practice.

The outermost corneal epithelium may or may not be removed prior to ablation, and may be removed if desired either by mechanical abrasion or with ablation itself. The laser energy is then delivered either in pulses or continuous wave fashion to ablate and remove corneal tissue. The laser beam diameter is controlled by various apertures or by a computerized spot control scanner to provide the desired diameter of ablation D1. The diameter of the ablation may be varied from ease to case, depending on the procedure being performed, but it is usually greater in diameter than the critical central optically used zone of the cornea. Diameters may typically be in the range of 5–8 mm, though other diameters may sometimes be employed.

The depth of the ablation is T1, and is less than the total corneal thickness, (approximately 0.52 mm). This depth may vary depending on the type of surgical procedure being performed, but is usually decided on prior to commencing surgery, and will typically range from 0.15 mm to 0.30 mm. The circular disc of tissue to be removed is shown cross-hatched in FIGS. 1,2. The new spherical surface produced within the patient's cornea 3, called the bed, has a curvature approximately equal to the initial anterior curvature minus T1.

Figure 3:
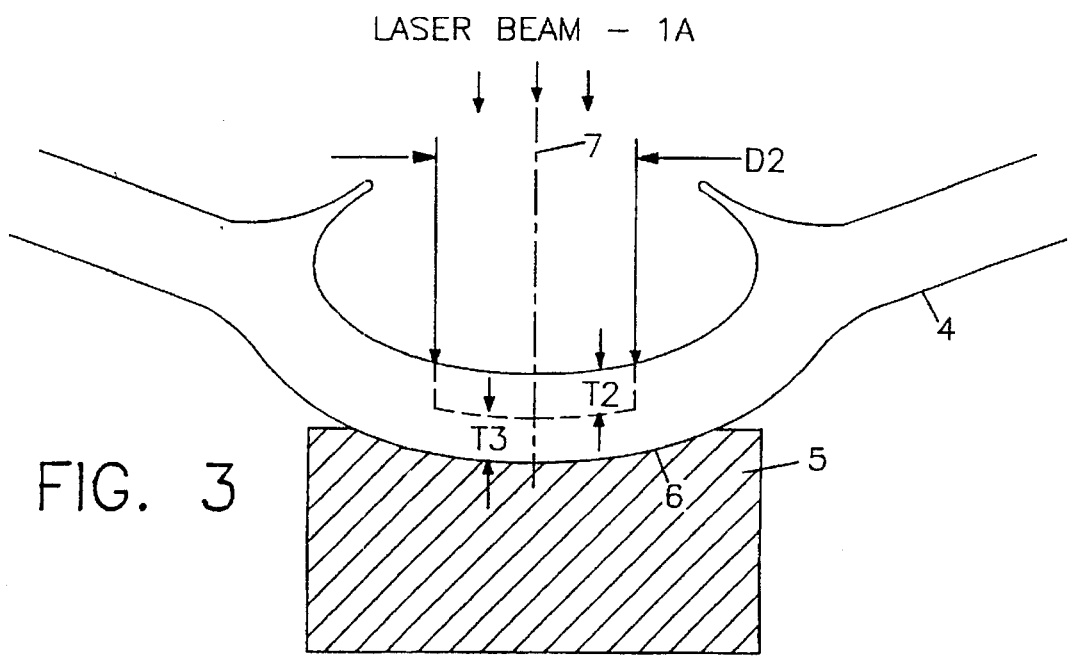
FIG. 3 is a view similar to FIG. 1 demonstrating an ablation in side view on a donor cornea.

FIG. 3 demonstrates the initial step in the production of a donor corneal disc with anterior membrane structure intact from a de-epithelialized donor cornea 4, shown with its posterior surface inverted or uppermost in the figure. This donor disc may be prepared by the surgeon or staff, or obtained commercially, as from an eye bank. The donor cornea is held stable within a concave block 5 of spherical curvature similar to that of the normal cornea. The donor cornea may or, may not have been treated in a corneal press or mold to restore it to normal dimensions and hydration by eliminating edema, or it may have been treated with a hypertonic solution or pressure to accomplish such. The surface of the block retaining the cornea may or may not have pores, suction or be made of a microporous substance, to hold the cornea in place, and the block is maintained in a stable position, as is currently done for excimer keratomileusis with the Summit laser, to allow accurate ablation.

Following stabilization, the donor cornea is exposed to the laser beam and energy delivered to its posterior surface to ablate away a circular disc of cornea, centered on the geometric center of the donor cornea 7, of constant thickness T2. The diameter of the circular ablated area is D2. Typically, D2 is the same as or slightly smaller (by about 0.5–0.7 mm to allow for changes in arc length in optical or refractive procedures) in diameter than its proposed recipient site (diameter D1) produced in FIG. 1. The depth of tissue to be removed, T2, is determined from the total donor thickness minus the proposed depth of resection thickness on the patient, T1, such that the residual thickness of the central donor following ablation, T3, is approximately 0.05–0.07 mm less than the recipient depth, T1, in FIG. 1, to accomodate forthcoming epithelialization which will increase thickness. Since only the posterior surface of the donor cornea is ablated, the anterior surface of the donor cornea is left intact.

FIG. 3 prepares the necessary final thickness and diameter of the donor tissue to be transplanted but does not isolate the disc from the peripheral cornea. This production of the final diameter of the donor disc can be accomplished as in FIGS. 4,5. In the preferred embodiment, FIG. 4, the disc is severed from its adjacent corneal rim by laser ablation. While maintaining the disc as in FIG. 3, the laser energy is no longer delivered to the central cornea upon reaching the ablation depth T2. Following this, the laser energy is delivered in a narrow annulus, concentric and contiguous to D2, of diameter D3, until the energy has ablated the annulus, of width (D3–D2)/2, to the total depth of the cornea, T2+T3. In thus manner, the central disc of thickness T3 and diameter D2 (cross-hatched) will now be freed of the corneal periphery, which is discarded.

Figure 5:
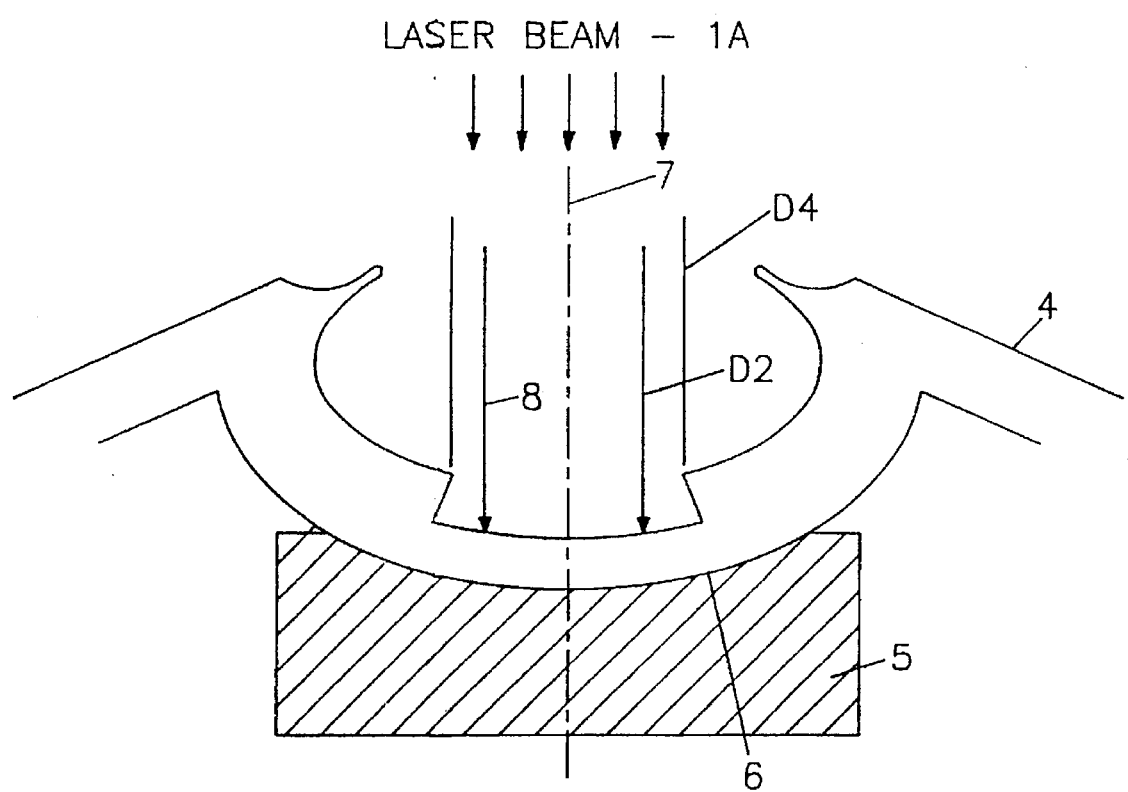
FIG. 5 is a view similar to FIG. 4 showing mechanical detachment of the donor corneal disc.

In FIG. 5, another embodiment is shown. Rather than use a laser to delimit the disc, it is delimited with a simple mechanical circular trephine blade, as is done in penetrating keratoplasty. In order to accomplish this, the diameter of the initial ablation in FIG. 3, is chosen to be significantly larger than the final desired disc diameter, D2, perhaps by 1–2 mm. This is represented as D4 in FIG. 5. This allows for easy placement of the circular trephine blade 8 of diameter D2 (or in some cases, like myopic corrections, slightly less), to delimit the disc from the periphery, which may be accomplished on block 5 or another block as is done in penetrating keratoplasty.

Figure 6:
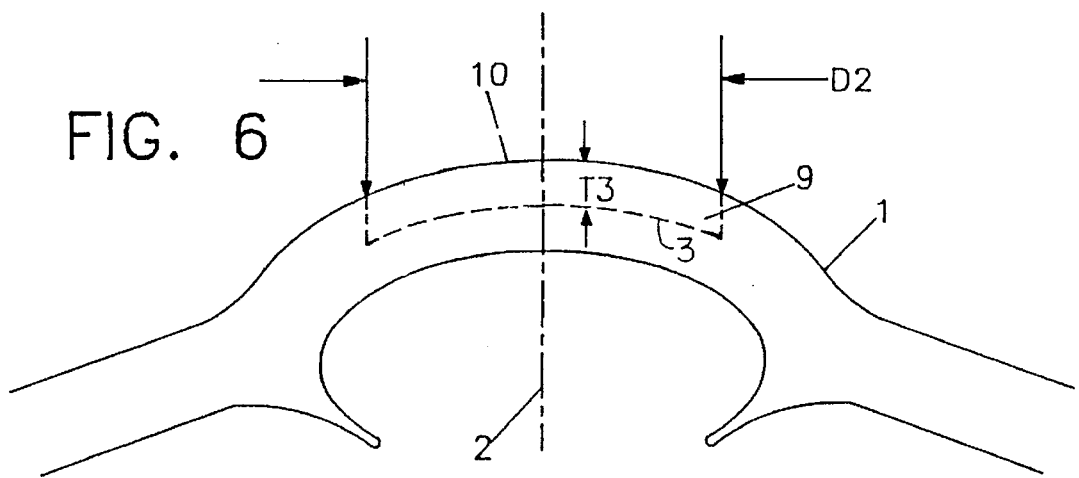
FIG. 6 is a similar view showing the reconstruction of the patient cornea.

FIG. 6 shows in side view the reconstruction of the patient's cornea following lamellar keratoplasty or phototherapeutic keratectomy. The donor disc 9 is placed with its stromal surface down against the exposed stromal surface of the patient's corneal bed 3. The final counsel thickness is thus approximately the same as it was prior to surgery. This provides for a smooth and normal anterior corneal contour 10 with a normal anterior. membrane complex, derived from the donor eye, in the central optic zone area. The donor disc can be fixated by sutures, adhesive, or other means. It may be covered by a soft contact lens or collagen shield to aid epithelialization.

Figure 4:
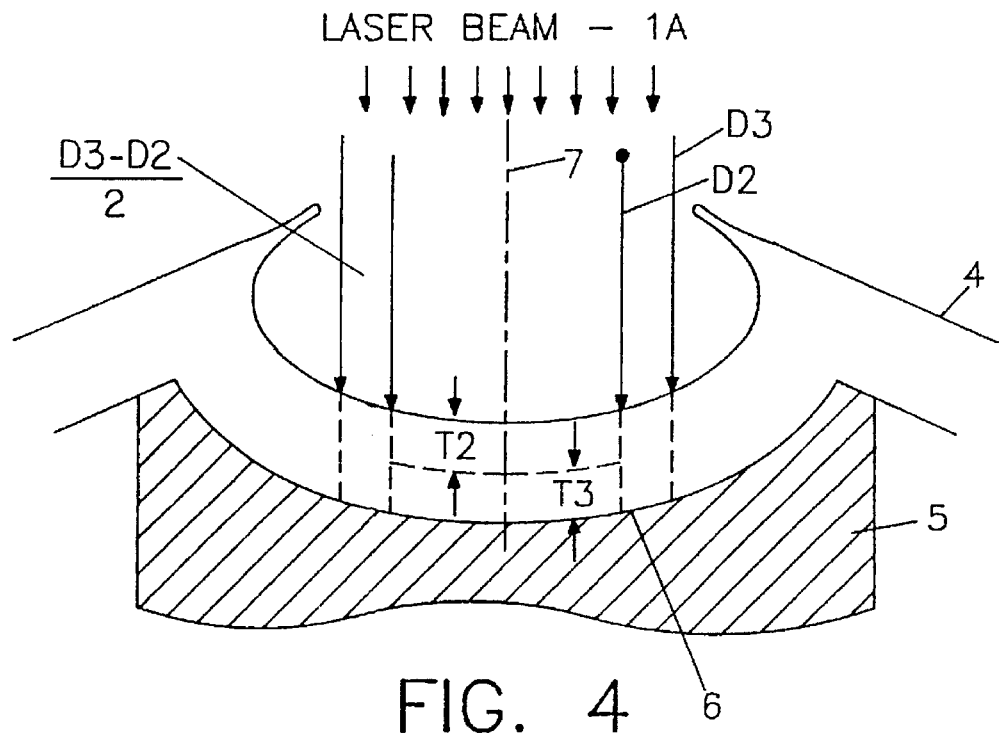
FIG. 4 is a similar view demonstrating laser ablation to detach the donor disc from the peripheral donor cornea.
Figure 7:
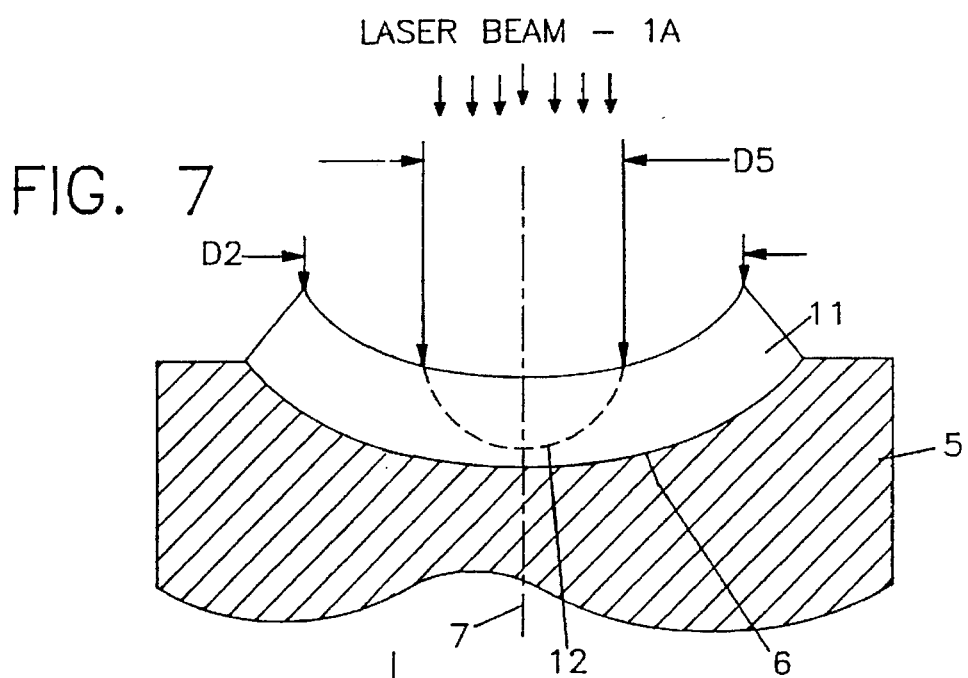
FIG. 7 is a similar view showing the use of the invention to produce a myopic correcting donor lenticule.

FIG. 7 describes how a donor disc containing optical power to correct myopia may be prepared from the resected donor disc prepared as per FIGS. 4,5 by secondarily exposing the cut stromal surface to the laser beam. Following delimitation of the disc as shown in FIGS. 4,5, the disc is once again seen in the holding block 5. The disc may or may not have been removed from the block after delimitation. In FIG. 7 the ablated bare stromal surface of the disc is further exposed to the laser beam in a controlled manner such that laser energy is selectively delivered, by any means, to be a maximum in the center of the disc and trails off to reach zero at diameter D5, D5 is thus the optic zone diameter of the lenticule 11, and is less than disc diameter D2. The laser energy is delivered in such a fashion such that a new spherical concave surface 12 results, circumferentially and symmetrically centered on the geometric center of the disc 7, and of shorter radius of curvature than the front surface of the dime 6. This myopic refractive lenticule is then placed onto the bed of the patient's cornea, am described for FIG. 6, with the stromal surfaces in contact. This allows for correction of a myopic refractive error in the patient with a normal anterior corneal structure in the central optic zone.

In the case of a synthetic material, the surgeon would buy the myopic lens already made to the requisite dimensions and refractive power, or one could make the powered lens from a parallel faced blank as in FIG. 7. In some cases, a peripheral rim or flange would insert into an undermined lip of the patient's peripheral cornea as described later in FIG. 12. This lens is fixated with peripheral sutures either in the lens or overlying it as a bridge, or with a peripheral adhesive. It is also covered with a soft contact lens or collagen shield.

Figure 8:
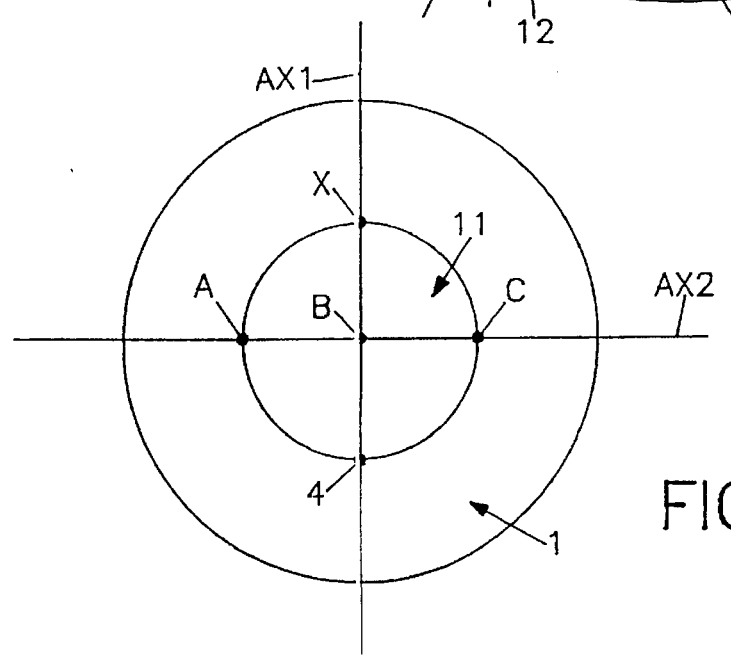
FIG. 8 is a view similar to FIG. 2 demonstrating orientation of surgical laser axis with respect to patient's optical astigmatic error.

The correction of astigmatism can also be described with FIG. 7. In this case, the ablated surface's profile 12 is a cross section of a cylindrical arc. This cylindrical arc extends the full length of the diameter of the ablation D5. This ablation pattern can be effected by commercially available lasers using an ablatable mask of appropriate dimensions, a diaphragmatic system which begins as a line and gradually expands as a slit with transverse symmetry about the axis of astigmatism, or by a computer directed scanning spot. The cylindrical area is described further in FIG. 8, a front view showing the cylindrical lens 11 already in place in the recipient cornea 1. Here, for example, if AX1 represents the axis of greatest refractive power in the patient's cornea and AX2 the axis with least power, it is desired to remove optical power and tissue from the refractive lens along axis XBY of the lens. Thus, the cylindrical ablation is such that the ablated concavity produced in the lens is maximum in depth and constant along line XBY and the depth varies along line ABC, with minima at points A and C for example. To produce the desired effect, it is thus important that the axis of the donor or synthetic lens be oriented appropriately along the axis of astigmatism of the patient's eye, such that axis XBY is aligned with AX1 of the patient. Such orientation may be ensured by placing a suture in the lenticule to mark the axis, or dye may be used to stain the axis. The lenticule is fixated as above for myopia. When synthetic material is used, the manufacturer will delineate the axis by appropriate means, such a such as a faint line in the periphery. Axes are easily determined and located during surgery by current devices and surgical technique.

The foregoing discussion applies also to correction of optical aberrations of the eye. In such cases, however, the profiles of the ablated zones may be other than circular.

In addition, for correction of combined refractive errors, the energy delivered by the laser will be a function of both the spherical (myopic or hyperopic) error and the astigmatic error to be corrected and will thus exhibit characteristics of both spherical and astigmatic ablation. Proper axis orientation need be maintained as described above.

For the correction myopia and presbyopia, for example, a multifocal lens system is created by appropriately distributing the laser energy throughout the optic zone such that the patient has clear vision both for distance and for near. This is accomplishable through concentric annular ablations with different curvatures or by producing a complex curve as is done for progressive bifocal lenses, where many focal points are created. Energy may be distributed by controlling diaphragms, by using an appropriately designed ablatable mask, or by use of a programmed computerized beam scanning device using a small spot.

For the correction of irregular astigmatism, with or without simultaneous correction of other optical problems, a corneal topographic map of the preoperative cornea is taken to allow determination of laser ablative energy distribution such that laser ablation will produce a new anterior curvature on the patient with the desired topography and optical power. The difference between the initial and final corneal shapes is analyzed by computer End a program determines the ablative energy distribution and levels. The laser delivers the energy through an appropriately designed ablatable mask as is now done for the Summit laser, determined with assistance of the computer, or delivered by a spot of energy, scanned across the cornea and directed by the computerized beam control device.

Figure 9:
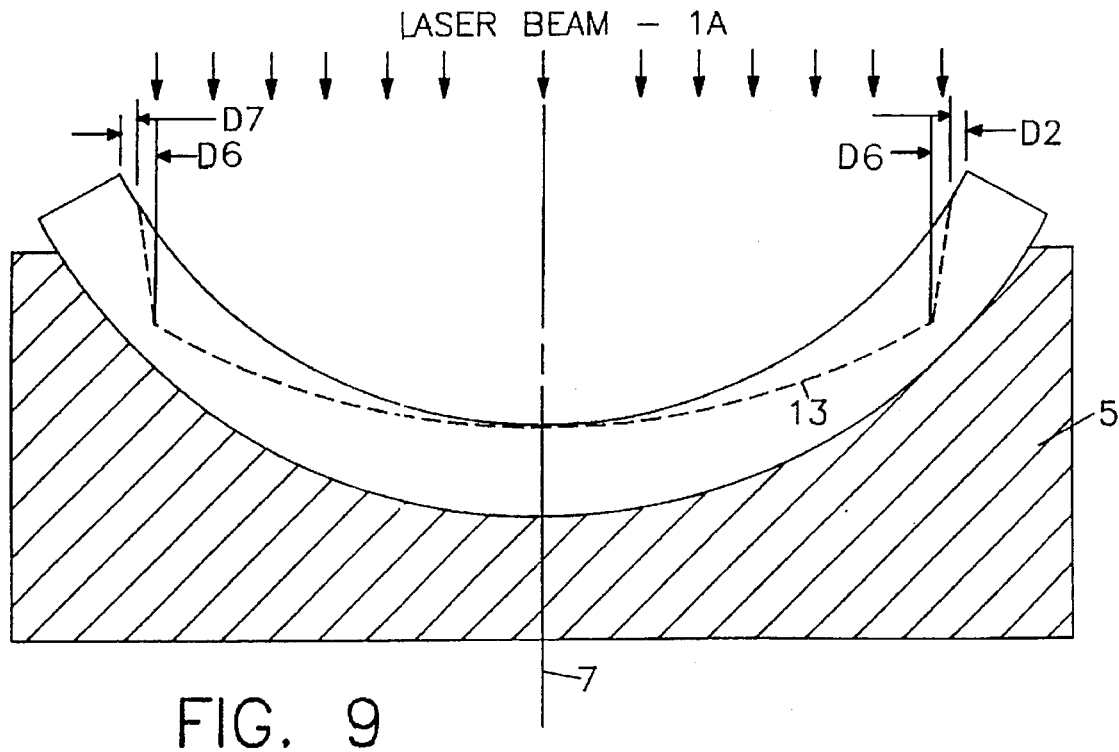
FIG. 9 is similar to FIG. 7 but for the production of a hyperopic donor lenticule.

FIG. 9 describes the procedure of keratomileusis, as described in FIG. 7, but for the production of a hyperopic correcting lenticule. In this case, laser energy is selectively delivered more to the mid-periphery of the disc, with maximum deliverance to this area and minimum to the geometric center at 7. This create a new surface 13 whose radius of curvature is greater than that of the disc, which is the same 6 as the retaining surface in block 5. The diameter of optic zone D6, centered on the geometric center of the disc, is smaller than the diameter of the disc, and typically 4–6 mm. It is to be noted that the hyperopic ablation manifests a bevelled edge or taper. This allows for good coaptation at the border of the wound. Thus, the optic zone proper, defined by the new curvatue, has optic zone diameter D6, while the bevel or taper is accomplished by providing continuously less ablatiion as one moves peripherally from diameter D6 to final oblation diameter D7, where oblation is reduced to zero. This hyperopic refractive lenticule is then removed from the block and placed in the bed of the patient's ablated cornea, as described for FIG. 6, and shown in FIG. 14. The stromal surfaces are placed into contact with one another, leaving the anterior membrane complex intact anteriorly. The patient's cornea will now assume a new shape, with a radius of central curvature greater than it was prior to surgery. In the case of a synthetic lens, it is placed on the bed and anchored with the anchoring rim or flange, if used, and as described in FIG. 12 and fixated as described under treatment for myopia. This produces a similar increase in curvature as when donor tissue is used.

Figure 10:
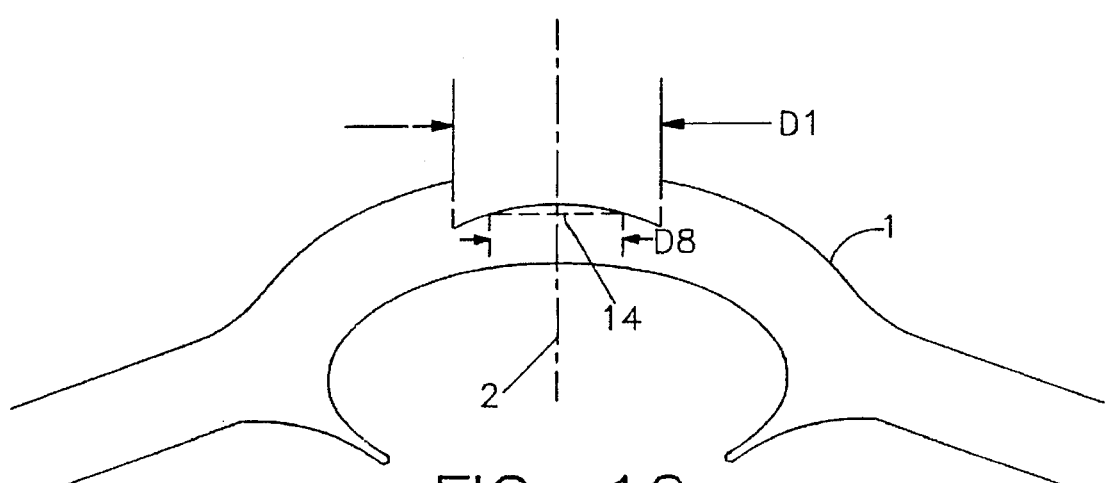
FIG. 10 shows in sectional view the use of the invention to correct myopia by modifying the patient's stromal bed.
Figure 11:
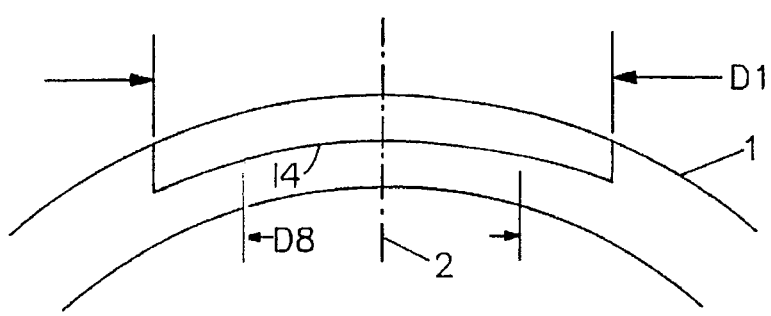
FIG. 11 shows in side view the reconstruction of the patient's cornea, as modified in FIG. 10, for myopic correction using a donor disc as produced in FIG. 3 or 4.

In FIG. 10, the preferred embodiment for correction of myopia is described. In this case a myopic correction is planned for the patient's cornea/eye, but instead of imposing the optic correction onto the posterior stromal surface of the donor disc, it is inscribed onto the cut stromal surface of the patient's exposed stroma 3 following the initial ablation of FIG. 1. After the initial ablation of FIG. 1, the laser is immediately reprogrammed, or has already had a program for the total procedure already installed, such that energy is further delivered to the ablated stromal surface 3 to create a new spherical surface, centered on the visual axis 2, of diameter D8, less than the initial ablation diameter D1. The radius of curvature of spherical convexity 14 is greater than that of the stromal bed 3. Thus, when a donor disc without optical power, as produced in FIGS. 3,4 or obtained from an eye bank or commercial company, is placed onto the bed, as shown in FIG. 11, its anterior surface receives the curvature transmitted from the modified bed, thereby providing the patient with a flatter cornea and correction of myopia. The disc is fixated as described above.

Similarly, for the correction of astigmatism or optical aberrations, a cylindrical or aberration correcting ablation, as described previously, is performed on the bed.

Figure 12:
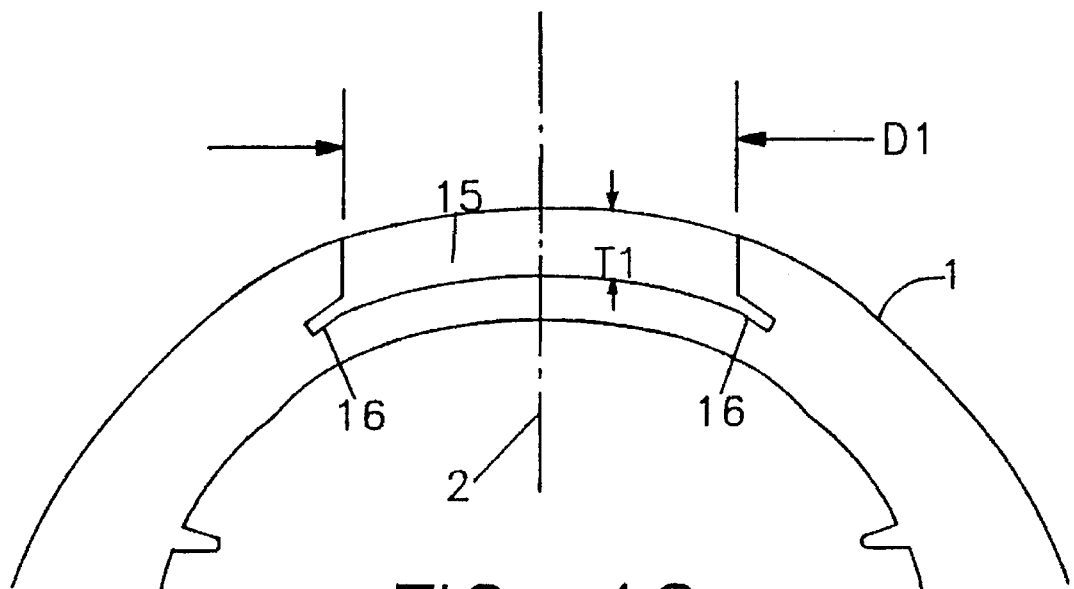
FIG. 12 is a similar view to FIG. 11, but employing a synthetic disc with an anchoring flange.

In addition, FIG. 11 is similar for cases using a synthetic material without optical power as is shown further in FIG. 12. This material 15, of appropriate dimensions D1 (or D1–0.50 mm) and T1, would most likely be purchased commercially, though it could be prepared in the fashion of FIGS. 3,4 from a starter blank. As synthetic material may be more difficult to safely fixate to the patient's cornea, it can be prepared with a small flange or rim at its lower surface to allow for insertion into a peripheral dissection at the level of the stromal bed 3. This arrangement is shown in FIG. 12, and accomplished as follows. After performing the ablation to depth T1, as in FIG. 1, the surgeon takes a spatula and inserts it at the level T1, flush with the bed, toward the periphery to undermine the anterior cornea of thickness T1 but peripheral to zone D1, for the entire 360 degrees. The radial extent of the undermining is typically 1–2 mm. Then, the synthetic lens is placed on the bed and the flange or rim 16 is placed into the potential space created to assist in anchoring the lens. The lens may be further fixated as described above.

Figure 13:
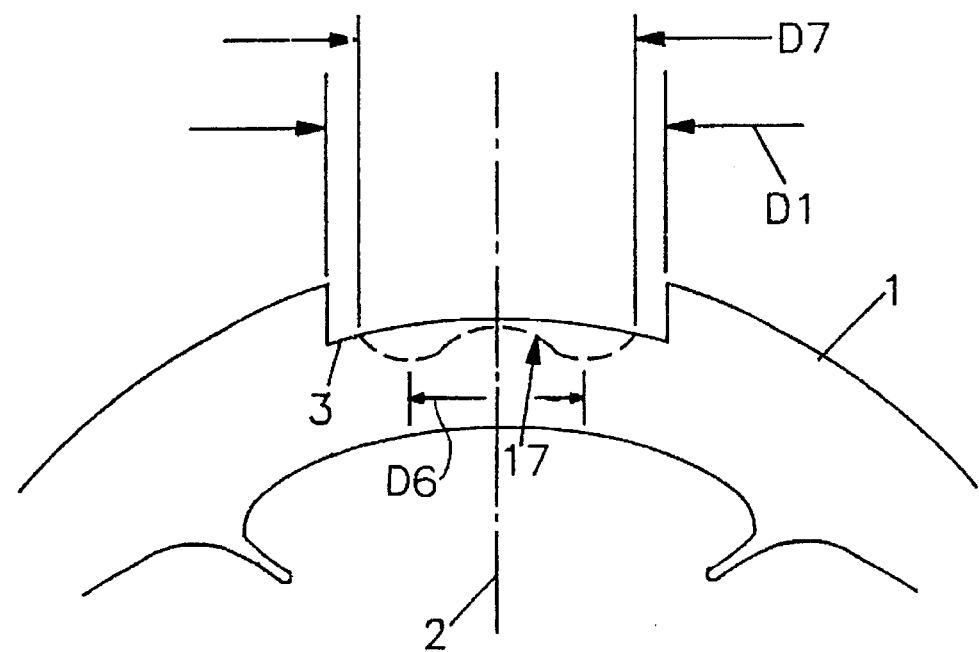
FIG. 13 shows a view similar to FIG. 10, but for correction of hyperopia.

In FIG. 13, a procedure similar to that described for FIG. 10 is carried out, only this time to produce a hyperopic correction, whereby the radius of curvature of surface 17 is less than that of the stromal bed 3. Optic zone diameter D6, centered on the visual axis 2 of the patient, is smaller than bed diameter D1. In addition, the functional optic zone diameter D6 is circumscribed by an annular zone of decreasing ablation of width (D7–D6)/2 as one moves peripherally to produce a taper or bevel. Following ablation, the donor or synthetic disc without refractive power is placed atop the ablated area, as shown in FIG. 14, with stromal side down in the case of donor tissue, such that the steepened curvature of the bed is transmitted to the anterior disc surface, thereby correcting hyperopia.

FIG. 15 describes a variant in which both donor tissue and synthetic material are employed. The patient's cornea 1 first undergoes ablation as in FIG. 1. The synthetic lens 18 of appropriate refractive power to correct the patients optical error, be it myopia, hyperopia, astigmatic, or any combination thereof, including correction for optical aberrations or other aspheric design, is placed onto the ablated surface 3. The donor disc 10 without optical power is then placed atop the synthetic lens, assumes a curvature similar to the synthetic lens, and thereby corrects the refractive error of the patient. In this case, the diameter of the synthetic lens D9 is made smaller than the diameters of the zonal ablation D1 on the patient and the donor disc D2 by approximately 1–2 mm to allow for better coaptation and subsequent wound healing.

I claim:

1. A method of optical surgery comprising the steps of:

ablating a patient's cornea by a controlled laser beam, to remove an outer portion, of a constant thickness, and having a diameter, and thereby expose a new surface of said cornea;

ablating a posterior surface of a donor corneal disc, leaving an anterior surface of said donor corneal disc intact, so that the anterior surface of the donor corneal disc is preserved to make the donor corneal disc, of a second diameter and thickness similar to the diameter and the constant thickness of the outer portion removed from the patient's cornea; and placing the donor corneal disc on the exposed new surface, to replace the removed outer portion of the cornea.

2. A method according to claim 1 in which the ablated patient's cornea and the donor corneal disc form a corneal assembly, in which said forming imposes optical power on said assembly, said power in the form of a curvature correcting optical dysfunctions, said dysfunctions selected from a group consisting of myopia, hyperopia, astigmatism, irregular astigmatism, optical aberrations, presbyopia, and combinations thereof.

3. A method according to claim 1 in which the placement of the donor disc on the cornea forms a corneal assembly, said forming imposes optical power on said corneal assembly, said optical powers imposed by curvatures which impose a plurality of focal points.

4. A method of optical surgery comprising the steps of:

ablating a patient's cornea by a controlled laser beam, to remove an outer portion of constant thickness, and having a diameter, and to thereby expose a new surface of said cornea, and to create an opening, over said exposed new surface, in the cornea;

creating a donor corneal disc, of diameter and thickness similar to the diameter and thickness of the outer portion removed from the patient's cornea;

imposing optical power onto a bare stromal surface of the donor corneal disc by laser ablation of a posterior surface of said donor corneal disc, such that an anterior surface of said donor corneal disc is preserved;

placing the donor corneal disc into the opening created in the patient's cornea.

5. A method of optical surgery comprising the steps of:

ablating a patient's cornea by a controlled laser beam, to remove an outer portion, of constant thickness, and having a diameter, and thereby expose a new surface of said cornea;

imposing optical power onto the surface by ablating the exposed new surface;

ablating a posterior surface of a donor corneal disc, leaving an anterior surface of said donor corneal disc intact, so that the anterior surface of the donor corneal disc is preserved, to make the donor corneal disc, of a second diameter and thickness similar to the diameter and the constant thickness of the outer portion removed from the patient's cornea; and placing the donor corneal disc on the exposed new surface, to replace the removed outer portion of the cornea.

6. A method according to claim 5 in which the step of ablating the patient's cornea comprises the steps of:

ablating the patient's cornea by a laser of uniform intensity to remove the outer portion of constant thickness, in an original ablation, and thereby expose the new surface of said cornea, prior to;

imposing optical power onto the new surface by ablating the exposed new surface in a zone of smaller diameter than the original ablation.

7. A method according to claim 5 in which the step of ablating of the patient's cornea includes:

first imposing optical power onto an old outer surface of the patient's cornea by ablating the old outer surface; prior to ablating the patient's cornea by a laser to remove a circular outer portion of constant thickness, and thereby expose a new surface of said cornea, said new surface having substantially the same optical power as was just imposed on the old outer surface.

8. A method of lamellar keratoplasty optical surgery comprising the steps of:

ablating a patient's cornea by a controlled laser beam, said beam removing an outer portion of constant thickness, and thereby exposing a new surface of said thickness, and thereby exposing a new surface of said cornea, and creating an opening, over said exposed new surface, in the cornea;

creating a donor corneal disc, of diameter and thickness substantially the same as the diameter and thickness of the removed outer portion removed from the patient's cornea by removing a posterior portion of the donors corneal disc, leaving an anterior portion of the donor corneal disc intact; and placing the donor corneal disc into the opening created in the patient's cornea.

* * * * *